United States Patent
Lamrani et al.

(10) Patent No.: US 11,471,597 B2
(45) Date of Patent: Oct. 18, 2022

(54) SYSTEMS, METHODS, AND APPARATUSES FOR UTILIZING CO-SIMULATION OF A PHYSICAL MODEL AND A SELF-ADAPTIVE PREDICTIVE CONTROLLER USING HYBRID AUTOMATA

(71) Applicant: Arizona Board of Regents on Behalf of Arizona State University, Scottsdale, AZ (US)

(72) Inventors: Imane Lamrani, Phoenix, AZ (US); Ayan Banerjee, Gilbert, AZ (US); Sandeep Gupta, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 570 days.

(21) Appl. No.: 16/593,337

(22) Filed: Oct. 4, 2019

(65) Prior Publication Data
US 2020/0108203 A1 Apr. 9, 2020

Related U.S. Application Data

(60) Provisional application No. 62/742,226, filed on Oct. 5, 2018.

(51) Int. Cl.
*A61M 5/172* (2006.01)
*G05B 13/04* (2006.01)
*G16H 20/17* (2018.01)

(52) U.S. Cl.
CPC ......... *A61M 5/1723* (2013.01); *G05B 13/042* (2013.01); *G05B 13/048* (2013.01);
(Continued)

(58) Field of Classification Search
CPC ............ A61M 5/1723; A61M 2202/07; A61M 2205/50; A61M 2205/52; A61M 2230/201; G16H 20/17; G05B 13/042; G05B 13/048
See application file for complete search history.

(56) References Cited

U.S. PATENT DOCUMENTS 9,619,213 B2   4/2017  Gupta et al.
9,626,521 B2   4/2017  Gupta et al.
(Continued)

FOREIGN PATENT DOCUMENTS

WO   WO-2016110804 A1 * 7/2016 ............... A61B 3/16

OTHER PUBLICATIONS

Althoff, M., et al., "Reachable set computation for uncertain time-varying linear systems," 14th International Conference on Hybrid Systems: Computation and Control , ACM (2011), pp. 93-102.
(Continued)

*Primary Examiner* — Tammara R Peyton
(74) *Attorney, Agent, or Firm* — Elliott Ostrander & Preston, P.C.

(57) ABSTRACT

Methods and systems for utilizing co-simulation of a physical model and a self-adaptive predictive controller using hybrid automata are described. For example, there is disclosed a self-adaptive predictive control system to generate an initial patient model with initial patient model settings $(k_1, k_2, \ldots, k_n)$ and execute a program that takes as input, the initial patient model settings as configuration parameters that specify at least a plurality of initial states. Such a system further receives new patient inputs and generates hybrid automata as a variation of the initial states by applying the new patient inputs to the initial patient model. The system further derives reachable states from the hybrid automata and outputs all reachable states computed. The system
(Continued)

further detects changes and responsively generates a new patient predictive model with new parameter settings ($k'_1, k'_2, \ldots, k'_n$), iteratively repeating until a termination criterion is satisfied. Other related embodiments are disclosed.

20 Claims, 11 Drawing Sheets

(52) U.S. Cl.
CPC ......... *G16H 20/17* (2018.01); *A61M 2202/07* (2013.01); *A61M 2205/50* (2013.01); *A61M 2205/52* (2013.01); *A61M 2230/201* (2013.01)

(56) References Cited

U.S. PATENT DOCUMENTS

| | | | |
|---|---|---|---|
| 9,642,543 | B2 | 5/2017 | Banerjee et al. |
| 9,706,963 | B2 | 7/2017 | Gupta et al. |
| 10,342,447 | B2 | 7/2019 | Banerjee et al. |
| 10,575,788 | B2 | 3/2020 | Gupta et al. |
| 10,671,735 | B2 | 6/2020 | Gupta et al. |
| 2013/0317377 | A1 | 11/2013 | Gupta et al. |
| 2018/0189678 | A1 | 7/2018 | Gupta et al. |
| 2019/0188587 | A1 | 6/2019 | Gupta et al. |
| 2019/0354087 | A1 | 11/2019 | Gupta et al. |

OTHER PUBLICATIONS

Andersen, K. E., et al., "A Bayesian Approach to Bergman's Minimal Model", Bishop, C. M. (Ed.) : Frey, B. J. (Ed.). Society for Artificial Intelligence and Statistics, (2003), pp. 236-243.
Chutinan, A., et al., "Computational Techniques for Hybrid System Verification". IEEE Transactions on Automatic Control, vol. 48, Issue 1, (2003), pp. 64-75.
Eren-Oruklu, M., et al., "Self-tuning controller for regulation of glucose levels in patients with type 1 diabetes," In American Control Conference, IEEE (2008), pp. 819-824.
Frehse, G., "Scalable Verification of Hybrid Systems" Systems and Control [cs.SY], Univ. Grenoble Alpes (2016), 118 pages.
Frehse, G., "Reachability of hybrid systems in space-time". ACM SIGBED EMSOFT (2015), 10 pages.
Frehse, G., et al., "SpaceEx: Scalable Verification of Hybrid Systems," Springer, Berlin, Heidelberg. 23rd CAV (2011), pp. 379-395.
Hatvani, L., "Formal Verification of Adaptive Real-Time Systems by Extending Task Automata," Diss. Mälardalen University, Västerås (2014), 47 pages.
Hovorka, R., et al., "Nonlinear model predictive control of glucose concentration in subjects with Type 1 diabetes,". Physiological Measurement vol. 25, No. 4 (2004), pp. 905-920.
Iftikhar, M. U., et al., "A Case Study on Formal Verification of Self-Adaptive Behaviors in a Decentralized System". arXiv preprint arXiv:1208.4635, (2012), pp. 45-62.
Jacklin, S., et al., "Verification, validation, and certification challenges for adaptive flight-critical control system software." AIAA Guidance, Navigation, and Control Conference and Exhibit (2004), 10 pages.
Lamrani, I., et al., "Co-simulation of Physical Model and Self-Adaptive Predictive Controller Using Hybrid Automata," In: Mazzara M., Ober I., Salaün G. (eds) Software Technologies: Applications and Foundations. STAF 2018. Lecture Notes in Computer Science, vol. 11176. (Dec. 2018) Springer, Cham, pp. 69-76.
Lamrani, I., et al., "HyMn: Mining Linear Hybrid Automata from Input Output traces of Cyber-Physical Systems," IEEE International Conference on Industrial Cyber-Physical Systems (2018), pp. 264-269.
Larsen, K. G., et al., "UPPAAL in a nutshell". International Journal on Software Tools for Technology Transfer vol. 1, Issue 1-2 (1997), pp. 134-152.
Moon, In-Ho, et al., "Approximate Reachability Don't Cares for CTL Model Checking," IEEE/ACM ICCAD (1998), pp. 351-358.
Ravi, K. et al., "High-density reachability analysis," IEEE/ACM ICCAD (1995), pp. 154-158.
Sadeghi, K., et al. "Safedrive: An autonomous driver safety application in aware cities." IEEE International Conference on Pervasive Computing and Communication Workshops (PerCom Workshops), IEEE, 2016, pp. 1-6.
Sadeghi, K., et al., "Optimization of Brain Mobile Interface Applications Using IoT," 23rd International Conference on HiPC, IEEE, (2016), pp. 32-41.
Sadeghi, K., et al., "Permanency analysis on human electroencephalogram signals for pervasive Brain-Computer Interface systems." EMBC 39th Annual International Conference of the IEEE (2017), pp. 767-770.
Tan, Li., "Model-based Self-Adaptive Embedded Programs with Temporal Logic Specifications," Sixth International Conference on Quality Software. IEEE (2006), pp. 151-158.
Turskoy, K., et al., "Adaptive control of artificial pancreas systems—a review," Journal of Healthcare Engineering vol. 5, No. 1 (2014), pp. 1-22.

\* cited by examiner

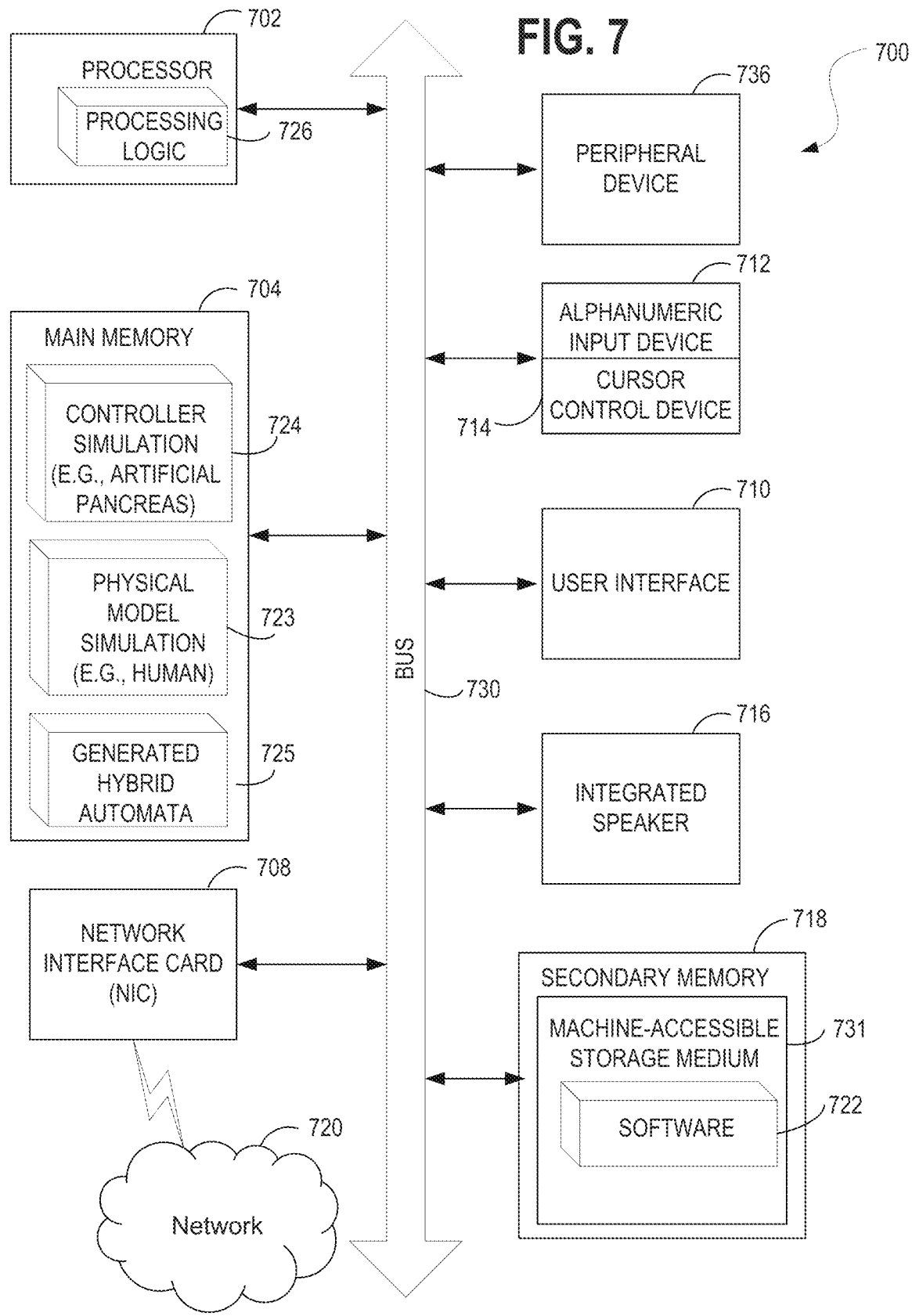

SYSTEMS, METHODS, AND APPARATUSES FOR UTILIZING CO-SIMULATION OF A PHYSICAL MODEL AND A SELF-ADAPTIVE PREDICTIVE CONTROLLER USING HYBRID AUTOMATA

CLAIM OF PRIORITY

This non-provisional U.S. Utility patent application is related to, and claims priority to the U.S. Provisional Patent Application No. 62/742,226, entitled "SYSTEMS, METHODS, AND APPARATUSES FOR UTILIZING CO-SIMULATION OF A PHYSICAL MODEL AND A SELF-ADAPTIVE PREDICTIVE CONTROLLER USING HYBRID AUTOMATA," filed Oct. 5, 2018, having, the entire contents of which are incorporated herein by reference.

GOVERNMENT RIGHTS AND GOVERNMENT AGENCY SUPPORT NOTICE

This invention was made with government support under 1116385 awarded by the National Science Foundation. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of healthcare apparatuses and self-adaptive prediction models, and more particularly, to systems, methods, and apparatuses for utilizing co-simulation of a physical model and a self-adaptive predictive controller using hybrid automata.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Within the context of control systems, so called adaptive control is the control method used by a controller which must adapt to a controlled system with parameters which vary or are initially uncertain. For example, as an aircraft flies, its mass will slowly decrease as a result of fuel consumption; a control law is therefore required which is enabled to adapt itself to changing conditions over time, with such conditions not being known ahead of time. In such a way, adaptive control is readily distinguished from robust control in that adaptive control requires no a priori information about the bounds of uncertain or time-varying parameters which may be encountered. Conversely, robust control guarantees that if the changes are within given bounds then the control law does not need to be modified, whereas adaptive control is concerned with the ability to self-change such control laws.

Taken a step further, Self-Adaptive Predictive (SAP) control delivers a promising approach to regulate Cyber-Physical Systems (CPS) which by their nature encounter changing conditions by adjusting the control parameters of such systems. In the medical and healthcare domains, self-adaptive control theory has gained increasing interest where emerging innovative medical devices adopt Self-Adaptive Predictive (SAP) control methodologies to deliver more accurate and personalized medical treatment to patients. For example, conventionally known artificial pancreas (AP) control systems simply are not capable of adjusting insulin administration based on a prediction pertaining to a patient's blood glucose levels, whereas Self-Adaptive Predictive (SAP) control mechanisms optimize control parameters based on feedback from the patients themselves, thus accounting for the ever-changing characteristics of their glycemic regulatory system.

Described herein are enhanced solutions to the problem of continually changing parameters, conditions, and characteristics of a system or mechanism being controlled, such as the exemplary artificial pancreas (AP) control systems. Notably, such parameters, conditions, and characteristics related to such systems simply cannot only be known in advance because it is unknowable how any particular medical patient's blood glucose levels will respond to various environmental conditions, and therefore, conventional AP control systems do not lend themselves to sufficient degrees of accuracy utilizing conventional predictive models, at least with respect to today's state of technology.

Problematically, application of control inputs and instructions to systems such as a conventional artificial pancreas (AP) and other devices in the medical field may potentially yield devastating results to a patient relying upon such a device due to the lack of sufficient accuracy. This problem is exhibited in the marketplace where it was only in late 2016 that the first so called artificial pancreas was approved by the FDA for Medtronic's "MiniMed 670G hybrid closed-loop system." Even with such approval, use of the device is restricted and the market has yet to see widespread adoption of this technology due in part to the complexities and associated risk of automating a life-sustaining medicine such as insulin.

Embodiments of the invention therefore improve the ability to deliver accurate inputs and instructions to such control systems which may thus in turn benefit patients which rely upon such devices in the medical and healthcare fields and may further benefit a larger population through the application of such improved control systems in a wide array of technical fields. Stated differently, the methodologies described herein provide pragmatic solutions to managing and controlling critical systems which by their nature are subject to unknown, ever-changing, and varying parameters, conditions, and characteristics, such as a human glycemic regulatory system for a patient with diabetes.

The present state of the art may therefore benefit from systems and methods for utilizing co-simulation of a physical model and a self-adaptive predictive controller using hybrid automata as is described herein.

BRIEF DESCRIPTION OF THE DRAWINGS

FIG. 7 illustrates a diagrammatic representation of a system for utilizing co-simulation of a physical model and a self-adaptive predictive controller using hybrid automata 700, depicted in the exemplary form of a computer system, in accordance with one embodiment.

DETAILED DESCRIPTION

Figure 1:
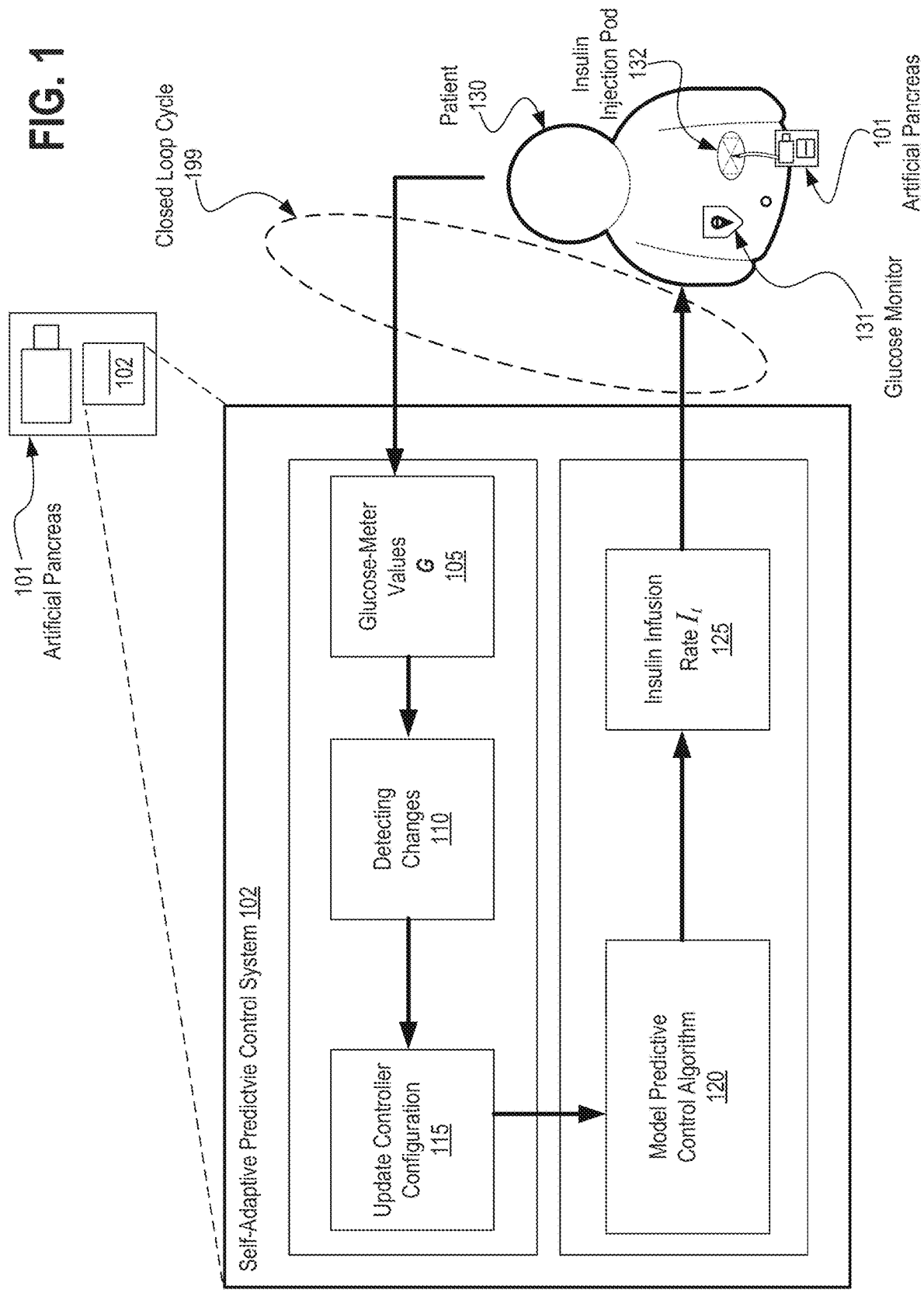
FIG. 1 depicts an exemplary artificial pancreas device managed by a self-adaptive predictive control system, in accordance with described embodiments.

Described herein are methods and systems for utilizing co-simulation of a physical model and a self-adaptive predictive controller using hybrid automata. In automata theory, a hybrid automaton or hybrid automata (plural of automaton) is a mathematical model for precisely describing systems in which specially configured digital computational processes interact with analog physical processes, including biological processes of a human medical patient. In other disciplines, a hybrid automata model may be applied to embedded computing systems, mobile robotic systems, and other complex large scale systems having unknowable varying parameters, such as an air traffic control system.

Each hybrid automaton operates as a finite state machine with a finite set of continuous variables whose values are described by a set of ordinary differential equations. When combined with specification of discrete and continuous behaviors, the collection of hybrid automata enable dynamic systems having both digital and analog components to be modeled and analyzed. Often applied to safety-critical applications, hybrid automata models prioritize reliability as a core design principle, so as to elevate correctness and accuracy of any predictive output of the model as a paramount concern. Consider the criticality of an automated insulin injection into a diabetic medical patient or the accurate measurement and automated adjustment of core temperatures in a nuclear reactor, the consequences for which inaccurate control inputs could result in catastrophic harm.

Exemplary embodiments set forth below therefore describe self-adaptive predictive control systems, each having at least a memory and a processor therein to execute instructions. Such systems may further include means for generating an initial patient model with initial patient model settings ($k_1, k_2, \ldots, k_n$); means for executing a program that takes as input, the initial patient model settings as configuration parameters that specify at least a plurality of initial states, a sampling time, and any number of additional optional parameters; means for receiving new patient inputs responsive to executing the program with the initial patient model with the plurality of initial states; means for generating hybrid automata as a variation of the initial states by applying the new patient inputs to the initial patient model; means for computing, via the executing program, a plurality of reachable states derived from the hybrid automata and producing an output file containing all reachable states computed; means for detecting a change has occurred within the self-adaptive predictive control system and responsively generating a new patient predictive model with new parameter settings ($k'_1, k'_2, \ldots, k'_n$); means for iteratively repeating the computing of the plurality of reachable states and producing additional output files for each iteration containing all reachable states computed until a termination criterion is satisfied; and means for forming a final reach set from a union of all output files having therein all reachable states obtained with all controller configurations generated at runtime of the executing program as computed for every iteration.

Simulation-based modeling tools, such as Matlab and Simulink are often used to model and evaluate the design of medical devices with self-adaptive predictive control. Utilizing the Self-Adaptive Predictive (SAP) control methodologies as described herein, a controller is made to respond not only to the dynamics of the physical system but to additionally respond to the subtle changes in the dynamics over time. Such a system therefore introduces time variance into the models used for such analysis and design of SAP controllers. Such models may accommodate time variance of the parameters describing the physical system through a system of differential equations involving the parameters.

According to certain embodiments, safety verification of Self-Adaptive Predictive (SAP) based controllers relies upon verifying whether or not a certain unsafe set is reachable from a set of initial states. Such verification may be performed through a hybrid analysis of the co-variation of the inputs and outputs of the controller following a discrete control strategy and the time variation of the physical system parameters.

Therefore, if the physical model is time-invariant, the verification problem is often considered to be intractable. Techniques such as reachability analysis for the time-invariant case does not provide exact solutions and therefore, approximations are used. The time variance of the physical system models in SAP is an added complexity which further exacerbates the problem.

Heretofore, there has been very limited work on verification of SAP type controllers assuming time variance of the physical models. Even the simpler problem of co-simulation of SAP controllers and physical system had not previously been studied in extensive detail.

The methodologies utilized herein consider a variety of co-simulation techniques for SAP controllers which were then utilized to integrate a co-simulation architecture for use with future verification. For instance, described methodologies develop a complete verification methodology for SAP controllers by defining co-simulation as the time synchronized simulation of the SAP controller which has at least a discrete decision making module, a physical model update method, and exhibits physical system evolution.

In the following description, numerous specific details are set forth such as examples of specific systems, languages, components, etc., in order to provide a thorough understanding of the various embodiments. It will be apparent, however, to one skilled in the art that these specific details need not be employed to practice the embodiments disclosed herein. In other instances, well known materials or methods have not been described in detail in order to avoid unnecessarily obscuring the disclosed embodiments.

In addition to various hardware components depicted in the figures and described herein, embodiments further include various operations which are described below. The operations described in accordance with such embodiments may be performed by hardware components or may be embodied in machine-executable instructions, which may be used to cause a specialized and special-purpose processor having been programmed with the instructions to perform the operations described herein. Alternatively, the operations may be performed by a combination of hardware and software. In such a way, the embodiments of the invention provide a technical solution to a technical problem.

Embodiments also relate to an apparatus for performing the operations disclosed herein. This apparatus may be specially constructed for the required purposes, or it may be a special purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various customizable and special purpose systems may be used with programs in accordance with the teachings herein, or it may prove convenient to construct more specialized apparatus to perform the required method steps. The required structure for a variety of these systems will appear as set forth in the description below. In addition, embodiments are not described with reference to any particular programming language. It will be appreciated that a variety of programming languages may be used to implement the teachings of the embodiments as described herein.

Embodiments may be provided as a computer program product, or software, that may include a machine-readable medium having stored thereon instructions, which may be used to program a computer system (or other electronic devices) to perform a process according to the disclosed embodiments. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical), etc.

Any of the disclosed embodiments may be used alone or together with one another in any combination. Although various embodiments may have been partially motivated by deficiencies with conventional techniques and approaches, some of which are described or alluded to within the specification, the embodiments need not necessarily address or solve any of these deficiencies, but rather, may address only some of the deficiencies, address none of the deficiencies, or be directed toward different deficiencies and problems which are not directly discussed.

In addition to various hardware components depicted in the figures and described herein, embodiments further include various operations which are described below. The operations described in accordance with such embodiments may be performed by hardware components or may be embodied in machine-executable instructions, which may be used to cause a special-purpose processor programmed with the instructions to perform the operations. Alternatively, the operations may be performed by a combination of hardware and software, including software instructions that perform the operations described herein via memory and one or more processors of a computing platform.

FIG. 1 depicts an exemplary artificial pancreas 101 device managed by a self-adaptive predictive control system 102, in accordance with described embodiments.

As depicted here, there is a patient 130 (e.g., a human user 130) to which the artificial pancreas 101 is affixed, forming part of a closed loop cycle 199, or a feedback loop between the self-adaptive predictive control system 102 and the human user and patient 130. Within the self-adaptive predictive control system 102, there may be observed an initial input from the artificial pancreas 101 via the glucose meter values G at block 105, which then proceeds to block 110 for detecting changes, and then to block 115 to update the controller configuration. Processing then flows to block 120 to model the predictive control algorithm and then to block 125 where the insulin infusion rate $I_t$ is determined, and finally completing the closed loop cycle 199, control instructions and parameters are issued to the artificial pancreas 101 which responsively administers insulin as directed by the self-adaptive predictive control system 102 pursuant to the determined insulin infusion rate L.

There are different types of adaptive control systems, such as open-loop adaptive control systems, direct adaptive control systems or model reference adaptive systems, and self-tuning regulators.

With respect to self-tuning regulators, the controller automatically tunes its parameters to obtain some desired properties for a closed loop system. If the estimates of the process parameters change, then the self-tuning regulator updates the controller parameters from the solution of the controller design problem using these estimates. Plant parameters are estimated at every sampling time while controller parameters are updated every n samples, which is configurable based on the implementation.

Consider the following exemplary Self-Adaptive Predictive Control System for an Artificial Pancreas (AP) 101. Artificial Pancreas systems are considered safety-critical cyber-physical systems as they are used for automated control of blood glucose level for Type-1 diabetic patients. The aim of such systems is to maintain the prescribed level of blood glucose, and avoid hypoglycemic and hyperglycemic conditions and events (e.g., excessively low and excessively high blood sugar levels, respectively). These dangerous events happen as a result of an inaccurate infusion rate of insulin $I_t$. For example, a glucose concentration G above 180 mg/dl can lead to hyperglycemia whereas a low glucose level, for example, a level below 50 mg/dl can cause hypoglycemia.

Figure 2:
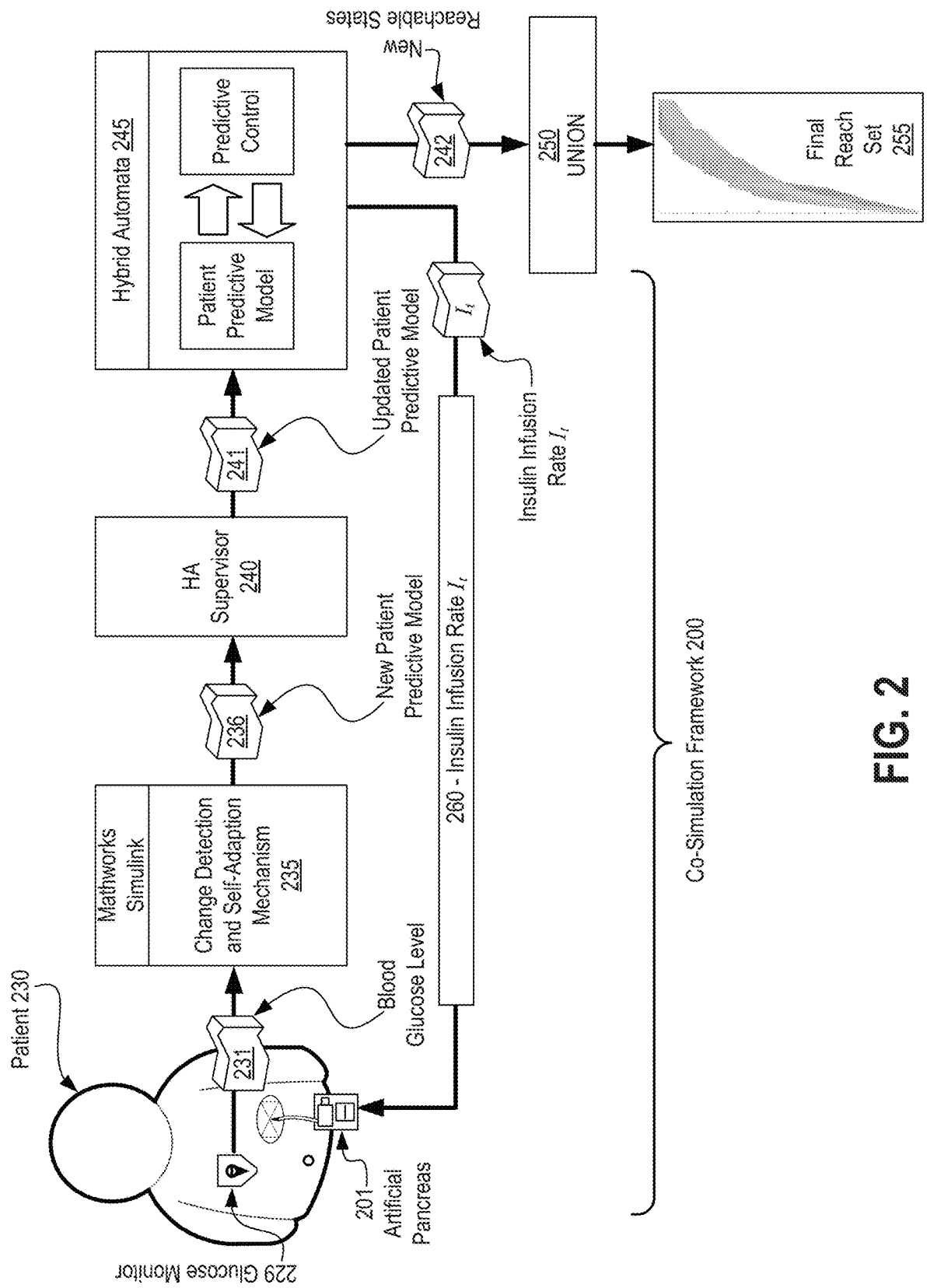
FIG. 2 depicts a new methodology utilizing a co-simulation framework in support of the embodiments described herein.

The self-adaptive predictive Artificial Pancreas 101, as shown at FIGS. 1 and 2, is communicably interfaced with the blood glucose monitor and sensor (e.g., element 131 at FIG. 1 and element 229 at FIG. 2) that measures a patient's glucose concentration. Such measurements are then provided to a communicatively interfaced self-adaptive predictive Artificial Pancreas 101 which embodies within its control hardware, a predictive control algorithm performed by the self-adaptive predictive control system 102 which estimates the value of the patient's blood glucose concentration either pursuant to or based upon the measurements from the communicatively interfaced blood glucose monitor 229 and sensor and then in turn computes the insulin infusion rate $I_t$ for actual insulin injection into the patient 130 via the connected insulin injection pod 132, with such an insulin infusion rate $I_t$ to be maintained until the next time step. In alternative embodiments, the blood glucose monitor 229 and sensor may be integrated within the Artificial Pancreas 101 apparatus and the communication interface between the Artificial Pancreas 101 and the blood glucose monitor 229 and sensor would thus be transmitted via an internal communications bus.

Different conditions, including meal consumption and physical activity, can trigger tremendous changes in the parameters of the predictive model describing blood glucose and insulin interaction.

The model is therefore non-linear in nature and is used by the controller to predict the value of blood glucose 30 minutes ahead in time. The model thus outputs the right amount of insulin infusion rate $I_t$ for the infusion pump to maintain until the next time step. Therefore, adjusting controller parameters in response to disturbances or systemic changes is a promising approach to regulate the Artificial Pancreas 101 and to achieve improved control of blood glucose levels for Type-1 diabetic patients.

Model checking by the Artificial Pancreas 101 provides another technique to ensure the correctness of such a system by exploring all possible environmental states. Such a model checking approach permits the Artificial Pancreas 101 to ensure that the system behaves as required in every state. However, conventionally known system models are not necessarily an accurate representation for time-invariant systems. Therefore, according to certain embodiments, the Artificial Pancreas 101 implements reachability analysis over hybrid automata which thus provides for a higher level of safety verification for time-invariant systems in accordance with such embodiments.

FIG. 2 depicts a new methodology utilizing a co-simulation framework 200 in support of the embodiments described herein.

As shown here, there is a co-simulation framework 200 implementation utilizing both Mathworks and SpaceEx, in which each executes simultaneously, however, alternative modeling platforms may be utilized.

Exact computation of reachable sets remains a difficult task and becomes even more complicated for time-varying systems. Therefore, a union 250 of short-term simulations on a set of initial conditions is performed in accordance with certain embodiments as an approach to compute over-approximation (see e.g., element 550 at FIG. 5) of reachable sets for time-varying systems. One approach to validate behavioral properties of decentralized self-adaptive systems operates by checking that the implementation of the system behaves in compliance with a specified model.

Therefore, as depicted here, it is in accordance with such embodiments that the self-adaptive system is modeled with timed-automata and required properties are specified using timed-computation tree logic. The model is then verified using UPPAAL (an abbreviation for the universities Uppsala University in Sweden and Aalborg University in Denmark which jointly developed the software). The UPPAAL validation suite provides a tool box for validation, via graphical simulation and verification, via automatic model checking.

Another formal verification approach of adaptive real-time systems to verify tasks schedulability uses adaptive tasks automata to model adaptive real-time systems and introduces affirmative schedulability predicates as part of the adaptive task automata to define the schedulability of a task. Tasks can be described in such a model so long as their behavior can be modeled using task automata. Such a methodology specifically defines decidability to prevent missed task deadlines when adjustments to the altered environmental conditions are performed.

An exemplary model therefore utilizes the following assumptions in accordance with described embodiments. First, adaptation scenarios must be predefined. Second, an environmental model should be available which specifies the failure events that are to be tested. Third, proper test selection must be defined since exhaustive testing of systems likely is not feasible. Previously available methodologies and validation approaches were unable to model and analyze SAP control systems embodying the above discussed approaches because adaptation scenarios cannot be predefined for SAP systems where the configuration functions are a linear combination between the parameters of the predictive model and the changing conditions of the environment. Moreover, an environmental model with changing characteristics is not available for conventional SAP control systems, and thus, previously available approaches are simply incompatible.

A model-based framework for developing self-adaptive systems is therefore utilized in accordance with certain embodiments, with such an approach introducing a configuration language to specify reconfiguration requirements and events triggering the reconfiguration. The configuration language is specified in temporal logic while the system behavior is depicted in the hybrid automata model of the system. Conventional reconfiguration mechanisms were limited to a constant function which can not be applied to predictive self-adaptive control systems where the configuration function is a linear combination between the parameters of the predictive model and the changing conditions of the environment.

A new approach is therefore required, such as the systems, methods, and apparatuses for utilizing co-simulation of a physical model and a self-adaptive predictive controller using hybrid automata as is described herein.

The new approach depicted here provides an alternative modeling technique for devices with self-adaptive predictive control. For example, such a methodology may leverage a SAP co-simulation framework for the self-adaptive predictive system embodied by the Artificial Pancreas (AP) described previously. Such a co-simulation framework thus implements the following methodology.

First, a new patient predictive model 236 is used to estimate the level of blood glucose 231 for the patient 230 thirty minutes ahead in time. Such time is configurable, but 30 minutes represents a common amount of time for a typical infused insulin to affect the patient's 230 biology. The patient predictive model 236 then computes the insulin infusion rate 260 which is to be maintained until the next time step. This model is represented by nonlinear equations 1, 2 and 3, below, where $\dot{X}$ represents the rate of the variation in the interstitial insulin concentration, where $\dot{G}$ is the rate of change of blood glucose concentration for the infused insulin concentration X, and where $\dot{I}$ is the variation in plasma insulin concentration.

$$\dot{X} = -k_2 X(t) + k_3 (I(t) - I_b), \quad (1)$$

$$\dot{G} = -X(t)G(t) + k_1 (G_b - G(t)), \quad (2)$$

$$\dot{I} = -k_4 I(t) + k_5 (G(t) - k_6) t. \quad (3)$$

Such a model contains parameters $k_1, \ldots, k_6$ that may be configurable tuned and adapted for accuracy purposes depending on the particular implementation. Some conditions including meal consumption, exercise, and emotional changes will be the underlying cause of these changes. The model therefore first derives an approximate linear system that matches closely with the real Artificial Pancreas (AP) system.

The change detection and self-adaptation mechanism 235 detects changes in the behavior of the human body (patient 230) using recent blood glucose measurements 231. These changes physically correspond to significant changes in glucose levels. The change detection and self-adaptation mechanism 235 compares the expected value of the new patient predictive model's 236 parameters and the vector of unbiased parameter estimates computed. An HA supervisor 240 then adapts and updates the new patient predictive model 236 to generate an updated patient predictive model 241 by re-estimating the changing parameters of the model using exclusively the more recent data provided in the form of the input rendered by the blood glucose level 231 from the actual patient 230.

The HA supervisor 240 is in the form of a python script and performs the following operations in accordance with certain embodiments:

First, the HA supervisor 240 generates an initial model file in SpaceEx's XML format with initial patient predictive model settings ($k_1, k_2, \ldots, k_n$), depicted here as the new patient predictive model 236 (e.g., a base or default patient model with default parameters not yet updated based on the actual patient's 230 blood glucose level 231 inputs). Next, the HA supervisor 240 calls the SpaceEx executable file to run the command line program that takes a model file in XML format and a configuration file that specifies the initial states, sampling time, and other options. The sampling time can be adaptively computed by the reachability analysis support functions or manually selected taking into consideration that a discrete transition should not occur between two consecutive sampling times The HA supervisor 240 then utilizes the SpaceEx executable to analyze the system and produces an output file $O_1$.txt containing the reachable states computed. Once a change is detected by the HA supervisor 240, it generates an updated patient predictive model 241 in the form of an XML file with new parameter settings ($k'_1, k'_2, \ldots, k'_n$). The HA supervisor 240 then proceeds to call the SpaceEx executable file to run the command line program with the newly generated model file. SpaceEx analyzes the system and produces an output file $O_2$.txt containing the reachable states, shown here as new reachable states 242. The HA supervisor 240 continues such processing until termination criterion is satisfied.

The final reach set of the self-adaptive control system is a union 250 of all reachable states obtained with all controller configurations generated at runtime resulting in the final reach set 255 depicted here, representing all reachable states pursuant to the analysis.

As can be seen here, the insulin infusion rate $I_r$ 260 is then looped back as input to the artificial pancreas 201 to facilitate actual insulin injection into the patient 230 via the connected insulin injection pod, which such an insulin infusion rate $I_r$ 260 being maintained until the next time step.

Figure 5:
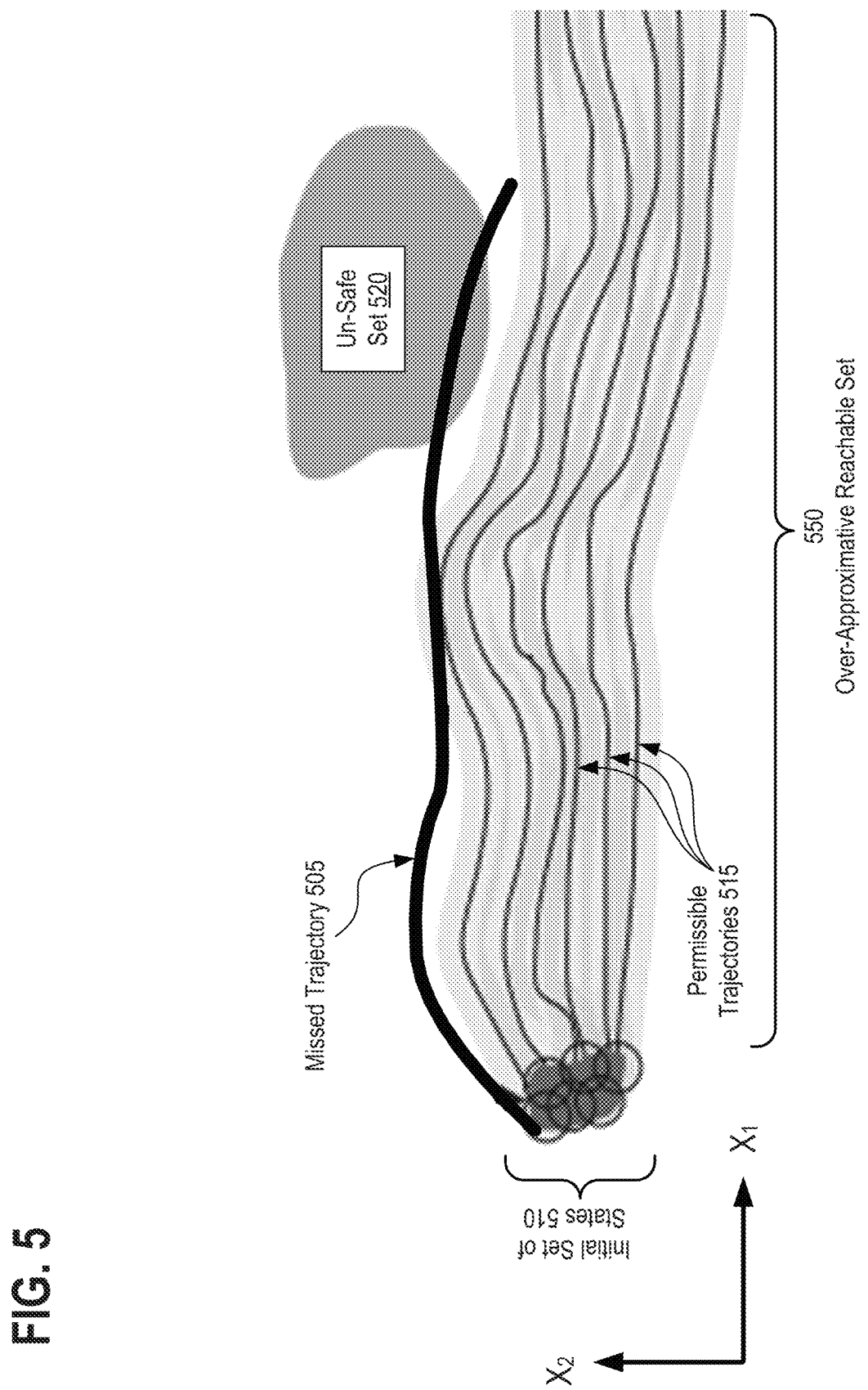
FIG. 5 depicts additional detail regarding the problem of a missed trajectory 505 in accordance with described embodiments.

Such an approach therefore supports modeling of predictive control systems using hybrid automata, and runtime self-adaption of hybrid automata based on new configurations from other modeling tools such as Simulink, while providing an alternative modeling technique for devices with self-adaptive predictive control and further enabling the verification of the safety of self-adaptive predictive control devices by checking whether the sets of reachable states of the system intersects with any unsafe set (see e.g., element 520 at FIG. 5).

Figure 3:
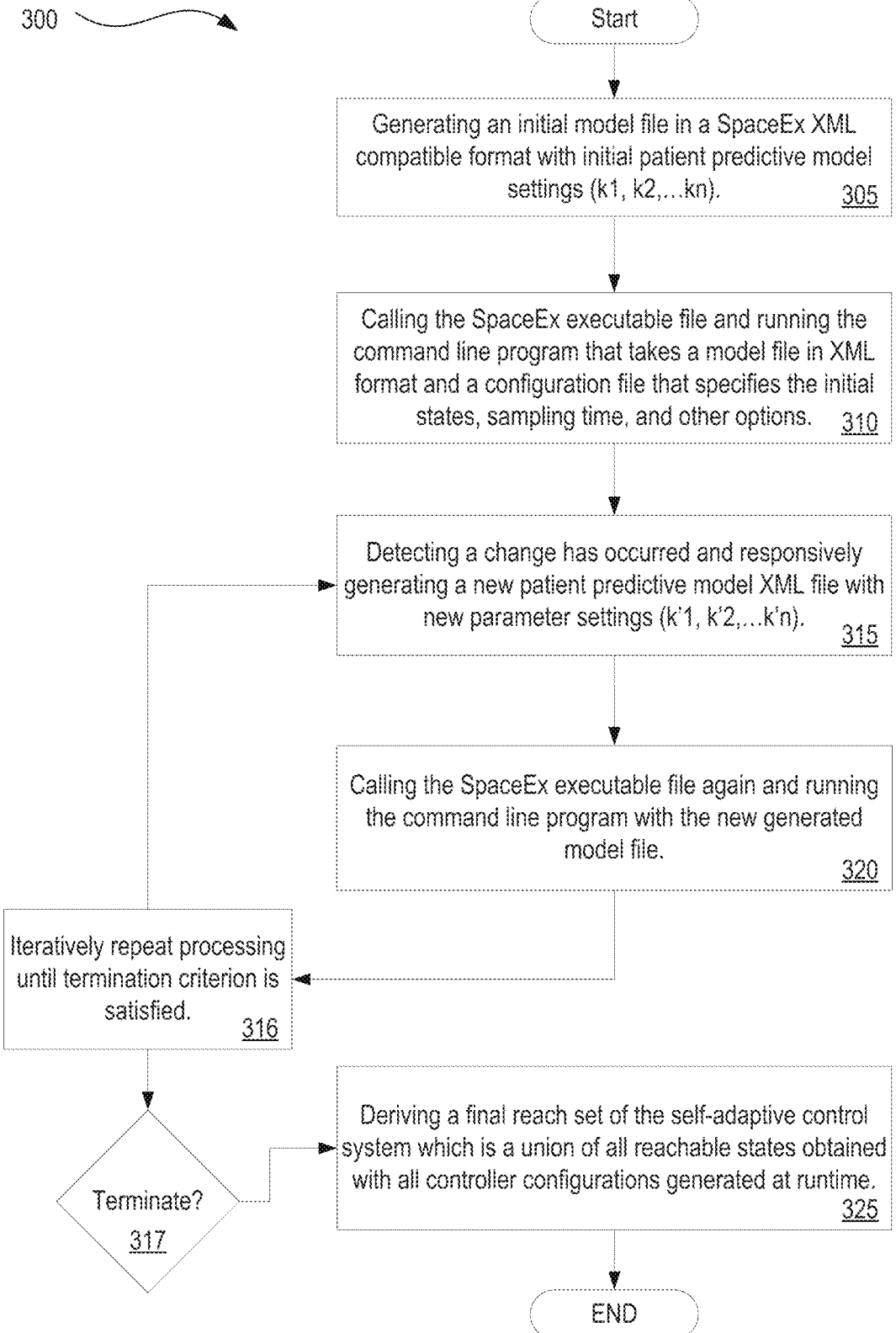
FIG. 3 depicts a flow diagram illustrating a method for utilizing co-simulation of a physical model and a self-adaptive predictive controller using hybrid automata within a computing environment such as a database system implementation supported by a processor and a memory to execute such functionality to provide on-demand functionality to users, customers, and subscribers, in accordance with described embodiments.

FIG. 3 depicts a flow diagram illustrating a method 300 for utilizing co-simulation of a physical model and a self-adaptive predictive controller using hybrid automata within a computing environment such as a database system implementation supported by a processor and a memory to execute such functionality to provide on-demand functionality to users, customers, and subscribers.

Method 300 may be performed by processing logic that may include hardware (e.g., circuitry, dedicated logic, programmable logic, microcode, etc.), software (e.g., instructions run on a processing device) to perform various operations such as generating, calling, detecting, repeating, deriving, terminating, operating, defining, declaring, associating, writing, receiving, retrieving, adding, transacting, training, distributing, processing, transmitting, analyzing, triggering, pushing, recommending, parsing, persisting, exposing, loading, storing, maintaining, creating, returning, presenting, interfacing, communicating, querying, providing, displaying, updating, sending, etc., in pursuance of the systems and methods as described herein. For example, the Artificial Pancreas 101 and its associated system and implementing hardware, such as the processor and memory of the system 700 as depicted at FIG. 7 and other systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

The method begins with processing logic at block 305 which generates an initial model file in a SpaceEx XML compatible format with initial patient predictive model settings ($k_1, k_2, \ldots, k_n$).

Processing logic at block 310 calls the SpaceEx executable file (e.g., using hybrid automata 245 at FIG. 2) to run the command line program that takes a model file in XML format and a configuration file that specifies the initial states, sampling time, and other options. According to such an embodiment, the sampling time can be adaptively computed by the reachability analysis support functions or manually selected taking into consideration that a discrete transition should not occur between two consecutive sampling times. For instance, utilizing SpaceEx, the processing logic analyzes the system and produces an output file $O_1$.txt containing the reachable states computed.

Processing logic at block 315, upon detecting a change has occurred, then generates a new patient predictive model XML file with new parameter settings ($k'_1, k'_2, \ldots, k'_n$).

Processing logic at block 320 calls the SpaceEx executable file again to run the command line program with the new generated model file. For instance, utilizing SpaceEx, the processing logic analyzes the system and produces an output file $O_2$.txt containing the new reachable states (FIG. 2, element 242).

Processing then advances to blocks 316 and 317 indicating that the processing is to iteratively repeat until termination criterion is satisfied, and then processing is to then terminate at block 317. If the termination criterion is not yet attained, then processing returns to block 315 for again detecting that a change has occurred and responsively generating another new patient predictive model with new parameter settings.

Processing advances to block 325 if the termination criterion has been attained, where processing logic at block 325 derives a final reach set (FIG. 2, element 255) of the self-adaptive control system which is a union (FIG. 2, element 250) of all reachable states obtained with all controller configurations generated at runtime.

Such a methodology therefore supports modeling of predictive control systems using hybrid automata, and runtime self-adaption of hybrid automata based on new configurations from other modeling tools such as Simulink as well as providing an alternative modeling technique for devices with self-adaptive predictive control capable of verifying the safety of self-adaptive predictive control devices by checking whether the sets of reachable states of the system intersects with any unsafe set (see again element 520 at FIG. 5). According to certain embodiments, the co-simulation framework may be defined as the time-synchronized simulation of a SAP controller's discrete decision making module with a physical model update method and further with the physical system's evolution.

According to a particular embodiment method 300 is performed by a self-adaptive predictive control system having at least a memory and a processor therein to execute instructions, in which the method includes: generating an initial patient model with initial patient model settings (k1, k2, . . . , kn); executing a program via the processor that takes as input, the initial patient model settings as configuration parameters that specify at least a plurality of initial states, a sampling time, and any number of additional optional parameters; receiving new patient inputs responsive to executing the program with the initial patient model with the plurality of initial states; generating hybrid automata as a variation of the initial states by applying the new patient inputs to the initial patient model; computing, via the executing program, a plurality of reachable states derived from the hybrid automata and producing an output file containing all reachable states computed; detecting a change has occurred within the self-adaptive predictive control system and responsively generating a new patient predictive model with new parameter settings (k'1, k'2, . . . , k'n); iteratively repeating the computing of the plurality of reachable states and producing additional output files for each iteration containing all reachable states computed until a termination criterion is satisfied; and forming a final reach set from a union of all output files having therein all reachable states obtained with all controller configurations generated at runtime of the executing program as computed for every iteration.

According to another embodiment of method 300, the initial model file and the new patient predictive model file are stored by the system in XML compatible format.

According to another embodiment of method 300, the sampling time is adaptively computed by reachability analysis support functions.

According to another embodiment of method 300, the sampling time is manually selected.

According to another embodiment of method 300, the sampling time is selected based on a requirement that a discrete transition must not occur between two consecutive sampling times.

According to another embodiment of method 300, the final reach set of the self-adaptive control system is a union of all reachable states obtained with all controller configurations generated at runtime of the executing program.

According to another embodiment, method 300 further includes: generating a safety report specific to a human patient modeled by the new patient predictive model; in which the safety report indicates a quality metric for the new patient predictive model with the new parameter settings reported as probability of the new patient predictive model maintaining a safe state for the human patient represented by the new patient predictive model and a probability of the new patient predictive model avoiding an unsafe state specifically for the human patient represented by the new patient predictive model.

According to another embodiment of method 300, the new patient predictive model with the new parameter settings form a personalized controller model unique to the human patient represented by the new patient predictive model.

According to another embodiment of method 300, the probability of the new patient predictive model avoiding an unsafe state specifically for the human patient represented by the new patient predictive model corresponds to a probability of the human patient represented by the new patient predictive model avoiding a hypoglycemic condition and avoiding a hyperglycemic condition when administered insulin by an artificial pancreas operating in accordance with the new patient predictive model with the new parameter settings.

According to a particular embodiment, there is a non-transitory computer readable storage media having instructions stored thereupon that, when executed by a processor of a self-adaptive predictive control system, the instructions cause the processor, to perform operations including: generating an initial patient model with initial patient model settings (k1, k2, . . . , kn); executing a program that takes as input, the initial patient model settings as configuration parameters that specify at least a plurality of initial states, a sampling time, and any number of additional optional parameters; receiving new patient inputs responsive to executing the program with the initial patient model with the plurality of initial states; generating hybrid automata as a variation of the initial states by applying the new patient inputs to the initial patient model; computing, via the executing program, a plurality of reachable states derived from the hybrid automata and producing an output file containing all reachable states computed; detecting a change has occurred within the self-adaptive predictive control system and responsively generating a new patient predictive model with new parameter settings (k'1, k'2, . . . , k'n); iteratively repeating the computing of the plurality of reachable states and producing additional output files for each iteration containing all reachable states computed until a termination criterion is satisfied; and forming a final reach set from a union of all output files having therein all reachable states obtained with all controller configurations generated at runtime of the executing program as computed for every iteration.

Figure 4A:
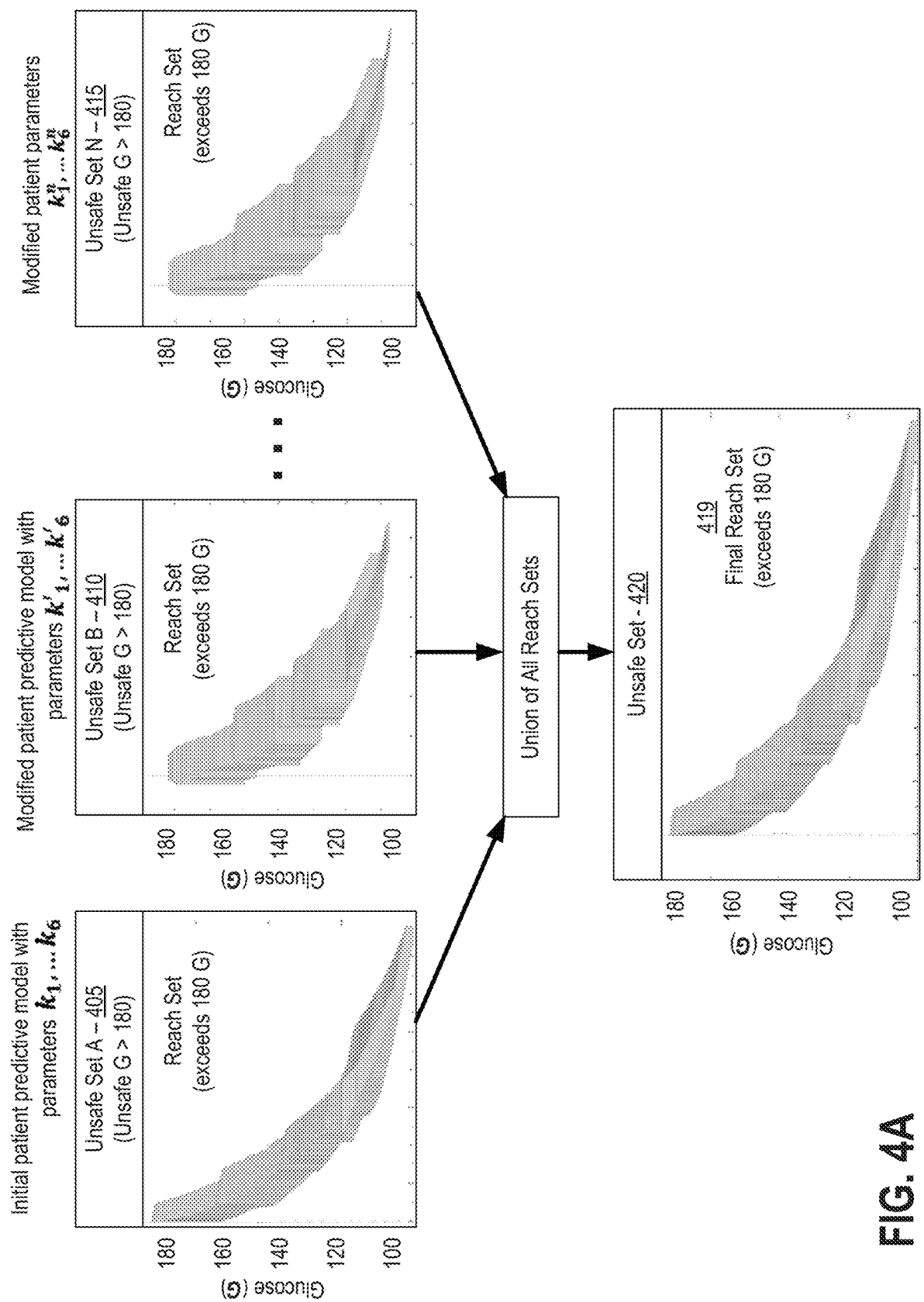
FIGS. 4A and 4B depict exemplary computation of reach sets for the artificial pancreas self-adaptive predictive control system resulting in a union of unsafe sets and safe sets respectively, in accordance with described embodiments.
Figure 4B:
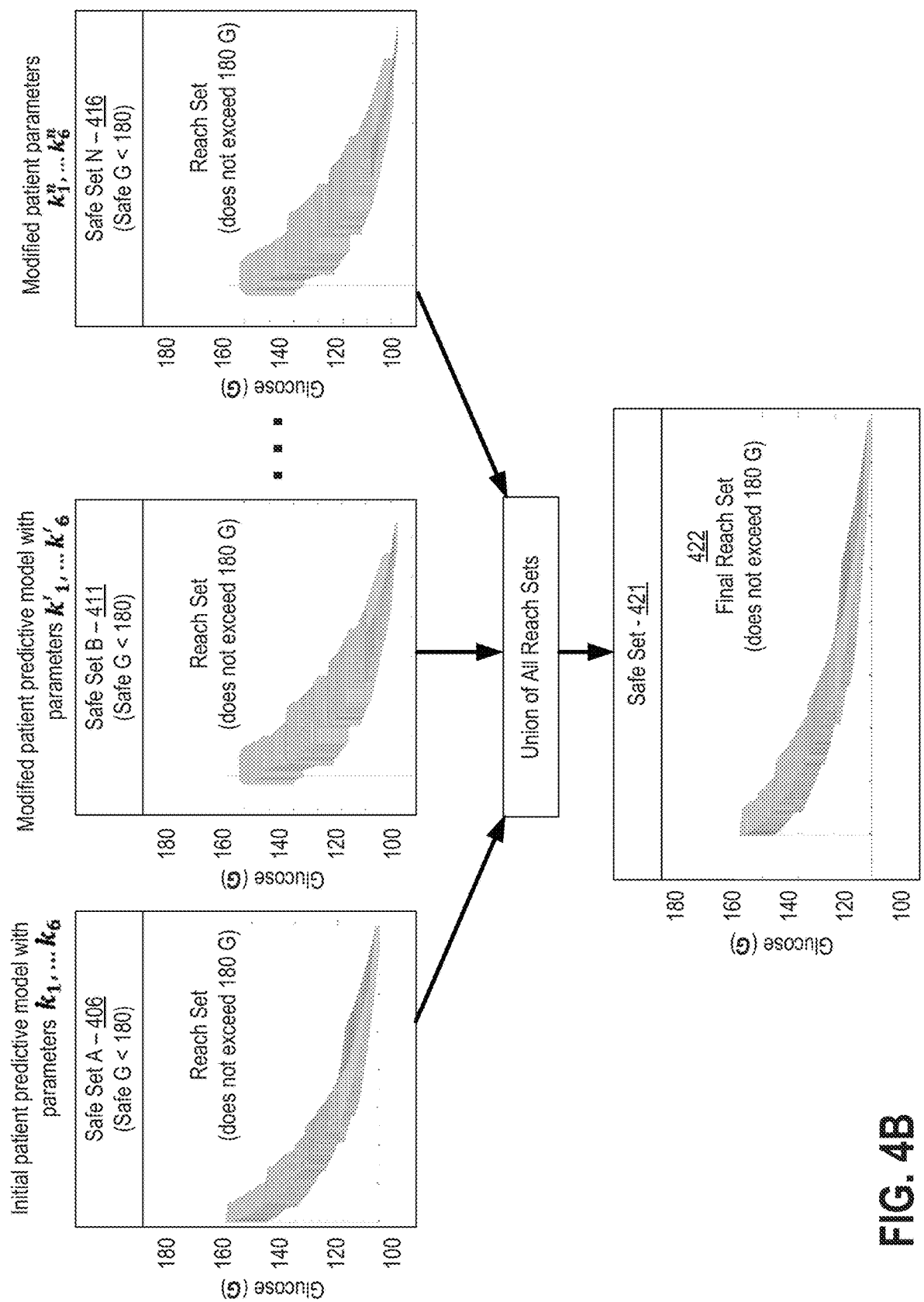

FIGS. 4A and 4B depict exemplary computation of reach sets for the artificial pancreas self-adaptive predictive control system resulting in a union of unsafe sets and safe sets respectively, in accordance with described embodiments.

With reference first to FIG. 4A, at every iteration of processing, a new controller configuration is generated and the reach set is computed accordingly. The final reach set 419 resulting in an unsafe set 420, is obtained by combining all the regions of the state space that the system has visited during every prior iteration of processing (e.g., each iteration of modifying the new patient predictive model with updated patient data to generate a reach set and looping back the determined insulin infusion rate $I_t$ and repeating until a termination criterion is met at which point the final reach set is derived).

As can be seen here, there are multiple unsafe sets including unsafe set A 405 providing the initial patient predictive model with parameters $k_1, \ldots, k_6$, unsafe set B 410 representing the modified patient predictive model with parameters $k'_1, \ldots, k'_6$, and unsafe set N 415 representing the modified patient parameters $k_1'', \ldots k_6''$, each of which result in a reach set which exceeds 180 G, and is therefore determined to be unsafe as the glucose level G exceeds to upper permissible bound for glucose concentration G at 180 mg/dl. Additional intermediate unsafe sets between unsafe set B at element 410 and unsafe set N at element 415 may permissibly be present. Similarly, there may be safe reach sets between unsafe set B at element 410 and unsafe set N at element 415 which do not exceed the upper bound for permissible glucose concentration G at 180 mg/dl, however, if any of the reach sets exceed glucose concentration G at 180 mg/dl then the resulting union of all reach sets will produce a final reach set 419 which exceeds 180 G, and is therefore an unsafe set 420.

As noted above, the final reach set 419 is obtained by combining all the regions of the state space that the system has visited to form the union of all reach sets resulting in the unsafe set 420 which represents the union or final reach set for all previously visited iterations.

With reference next to FIG. 4B, at every iteration of processing, a new controller configuration is generated and the reach set is computed accordingly, however, unlike in the prior example of FIG. 4A, the final reach set 422 as depicted at FIG. 4B results in a safe set 421, as it has been obtained by combining all the regions of the state space that the system has visited during every prior iteration of processing which includes only safe reach sets (e.g., specifically safe set A 406 with G less than 180, safe set B 411 with G less than 180, and safe set N 416 with G less than 180), none of which exceed 180 G, and thus, when the union of all reach sets is formed, the final reach set 422 similarly does not exceed 180 G, and is thus deemed to be a safe set 421 below the upper permissible bound for glucose concentration G at 180 mg/dl.

In such a way, the described methodologies address the problem of safety verification of self-adaptive control systems and set forth a novel approach to model and verify the safety of self-adaptive predictive control systems via reachability analysis and co-simulation. Reachability analysis is performed by taking into consideration the ever-changing characteristics of the system by updating the hybrid automata model of the system every time a new controller configuration is needed. By utilizing systems where controller configurations are not predefined, the described methodology institutes a run-time verification of the self-adaptive systems using reachability analysis. Thus, the described approach may additionally benefit further from or be combined with complementary methodologies for more accurately selecting appropriate termination criteria for the safety analysis.

FIG. 5 depicts additional detail regarding the problem of a missed trajectory 505 in accordance with described embodiments. In particular, the difference between numerical simulation vs. reachability analysis may be observed, in which numerical simulation is used to test the correct behavior of a system, providing the advantage of proving that system is unsafe (by producing a missed trajectory 505 that hits the unsafe set 520), whereas the disadvantage is that the trajectory that hits the unsafe set 520 may have been overlooked.

Reachability analysis determines the set of states that a system can possibly visit via the permissible trajectories 515 starting from a set of initial states 510. If the reachable set does not intersect with any unsafe set 520, then safety of the system is guaranteed via the method of computing over-approximative reachable sets for time-varying systems, as presented here. Such reachability analysis over hybrid automata may thus be selected in accordance with certain embodiments so as to attain a higher level of safety verification rigor.

FIGS. 6A, 6B, 6C and 6D depict the exemplary Artificial Pancreas (AP) in greater detail in accordance with described embodiments.

Utilizing Self-Adaptive Predictive (SAP) control, different conditions including disturbances or systemic changes which result in tremendous changes in the parameters of the predictive model describing the dynamics of the system may nevertheless be analyzed and systematically accommodated within a safe state set while wholly avoiding any risk of traversing an unsafe state. Adjusting controller parameters in response to these changes using SAP to regulate the system achieves improved control. Reachability analysis over hybrid automata provides a higher level of safety verification rigor. Existing hybrid automata tools simply do not support modeling of run-time self-adaption of predicates.

With reference to FIG. 6A, the patient 130 again sits in the middle of a feedback loop formed by the iterative processing of the artificial pancreas 101 which communicates input from the glucose monitor 131 initiating the processes with the glucose-meter value $B_g$ at block 615, with processing advancing to block 620 where the blood glucose monitoring control algorithm is executed by specially configured computing hardware such as a processor and a memory of the above described system which is capable of executing instructions in support of the glucose monitoring control algorithm. Processing then advances to block 625 where the insulin infusion rate $I_t$ is determined, at which point the determined insulin infusion rate $I_t$ is returned to the artificial pancreas which then infuses the determined dosage of insulin into the patient 130 via the insulin injection pod 132. All input/output operation traces 630 are tracked and monitored by the systems of the artificial pancreas with such data additionally being consumed by the new patient predictive model in accordance with certain embodiments to better tune the accuracy of the predictions by the artificial pancreas over time for this specific patient 130 based on how the actual patient's biology reacts to known quantities of insulin injections as controlled by the artificial pancreas.

Figure 6A:
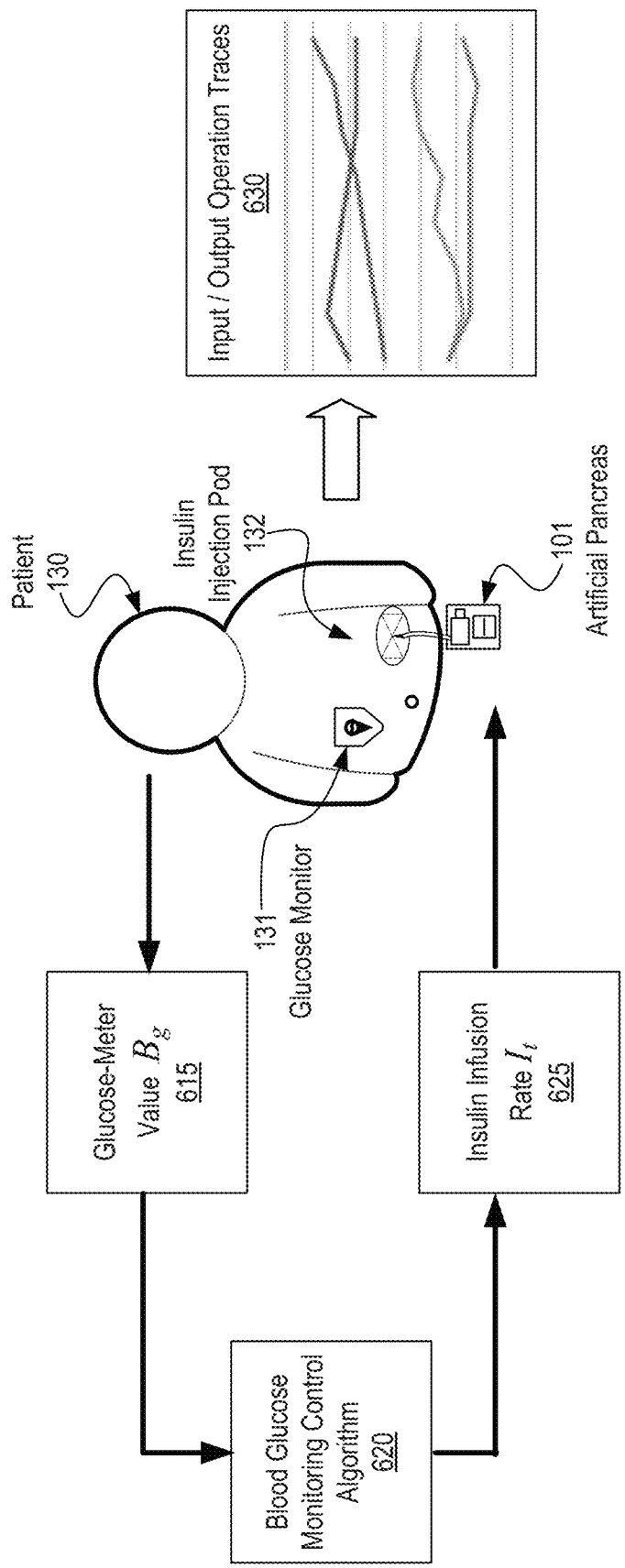
FIGS. 6A, 6B, 6C and 6D depict the exemplary Artificial Pancreas (AP) in greater detail in accordance with described embodiments.
Figure 6B:
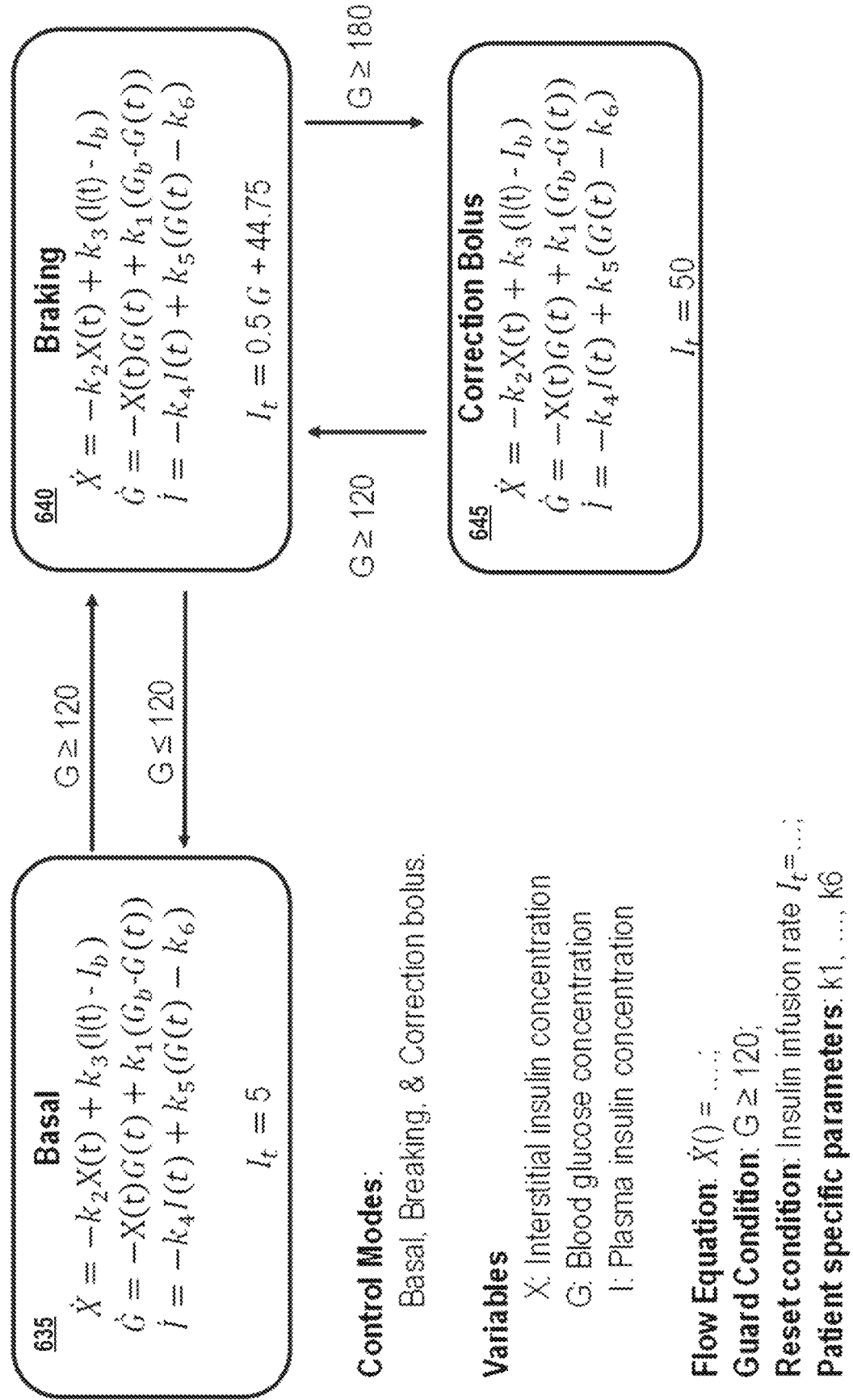

With reference to FIG. 6B, there are further depicted the various control modes for the artificial pancreas, including the basal control mode 635, a braking control mode 640, and a correction bolus control mode 645, which operate via the artificial pancreas to maintain blood glucose concentration levels of the patent within appropriate levels (e.g., within the generally accepted glucose concentration G range between 120 mg/dl and 180 mg/dl), or within another range as configured for the particular implementation.

The variables X, G, and I are depicted in which X represents the interstitial insulin concentration, G represents the blood glucose concentration, and I represents the plasma insulin concentration. Further defined for the various control modes 635, 640, and 645 are the flow equation, guard condition, resent condition, and the tunable patient specific parameters.

Figure 6C:
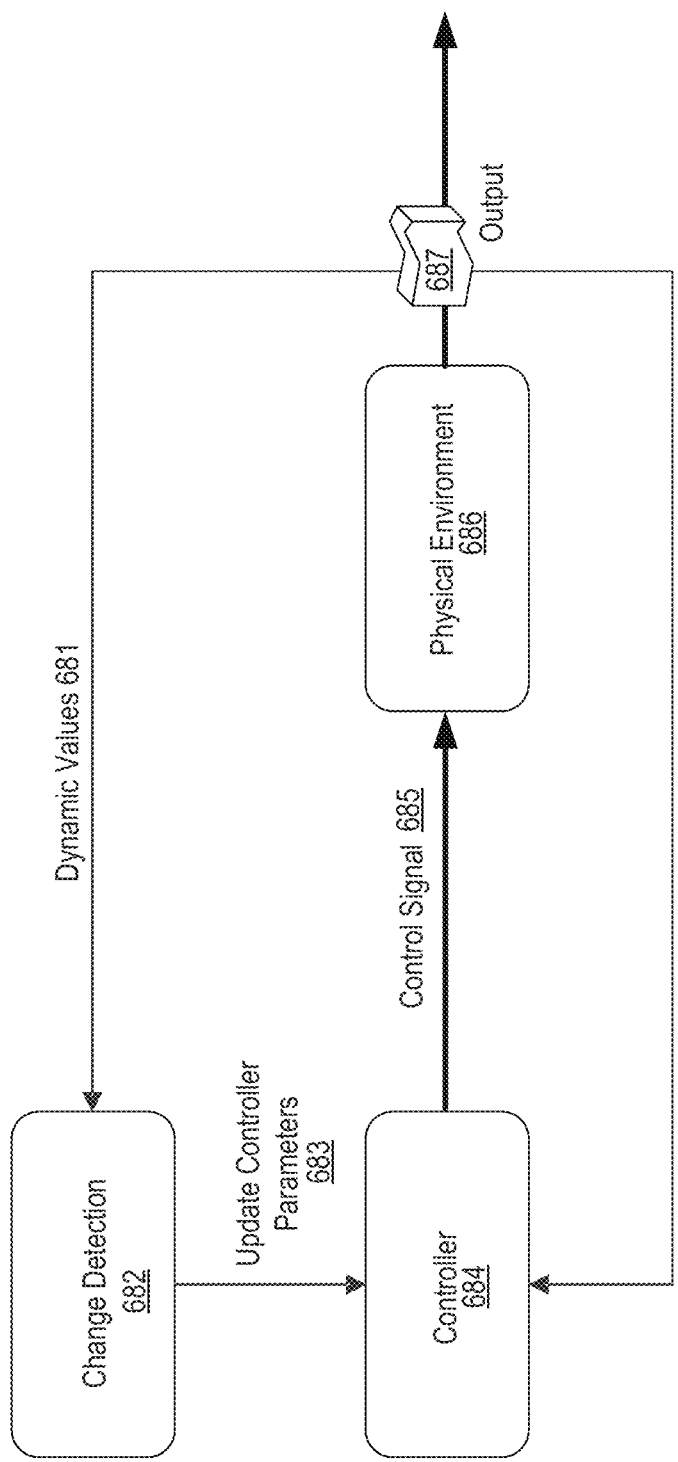

With reference to FIG. 6C, there is further depicted the feedback loop of the system in which the controller modifies itself in response to changes in the dynamics and characteristics of the system being controlled, thus producing the desirable feedback loop. As shown here, dynamic values 681 are input to the change detection 682 operation which triggers the system to update control parameters 683. The updated control parameters are input into the controller 684 which issues a control signal 685 to the physical environment 686, causing the infusion of insulin by the artificial pancreas responsive to an output 687 from the feedback loop (received as input at the artificial pancreas) and thus a change in the monitored blood glucose levels, which then in turn feeds dynamic values 681 back into the feedback loop and the controller for further iterative processing responsive to a continuously changing execution environment.

In such a way, practice of the described embodiments yield much a needed Safety-critical Cyber-Physical system (CPS) design and implementation with a new revolution of self-adaptation capabilities. Such Self-adaptive predictive control (SAP) systems configured to implement the described methodologies and supporting computing components will thus adjust their behavior in response to the continuously changing execution environment while achieving improved control. For example, medical devices which adopt the described self-adaptation control theory to deliver more accurate, personalized treatment to patients will outperform conventionally available units available to the marketplace today. Ideally, all such Safety-critical Cyber-Physical system (CPS) should ultimately be regulated and thus be required by law to embody verification techniques and to be equipped with self-adaptation capabilities for the protection of the patient. Reachability analysis provides one such versatile tool which may be utilized for such CPS verification.

Figure 6D:
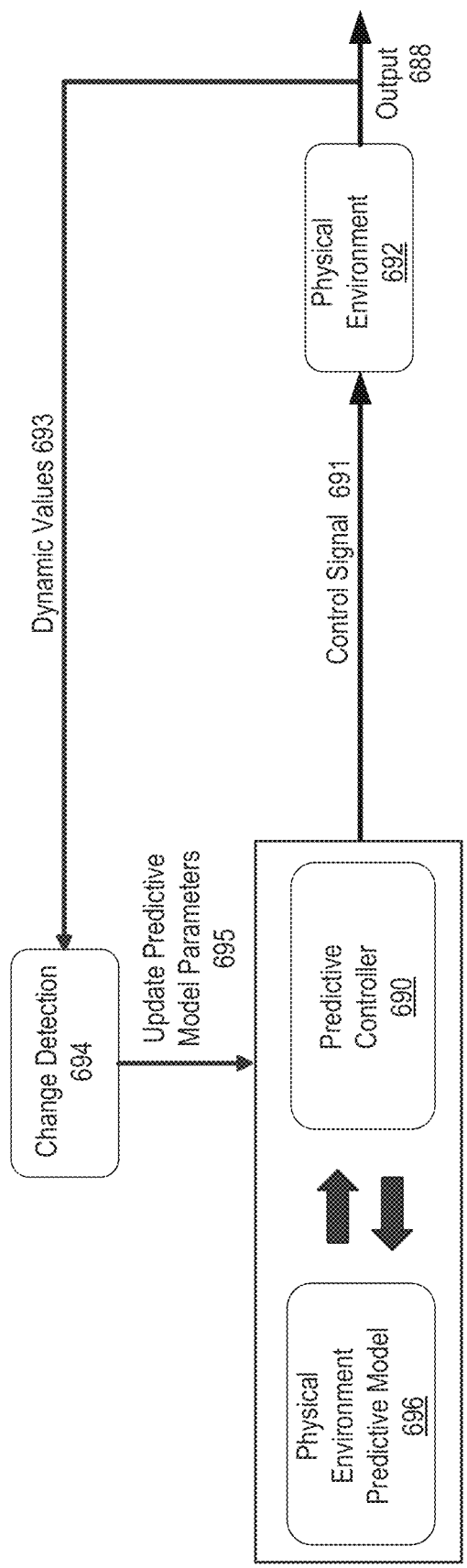

With reference to FIG. 6D, there is further depicted how the predictive model of the physical environment 692 is used to estimate the values the system dynamics, in which the predictive control algorithm as implemented by the predictive controller 690 computes its control signal 691 based on dynamically predicted values. As shown here, dynamic values 693 (e.g., actual patient measurements) are received into the feedback loop and processed at the change detection 694 block responsive to which updated predictive model parameters 695 are generated and input into the predictive controller 690 which responsively issues the control signal 691 to the physical environment 692 as an output 688 based on the updated predictive model parameters and also based on the physical environment predictive model 696 which operates cooperatively with the predictive controller 690.

According to such embodiments, the change detection 694 operation compares the expected value of the model parameters and the vector of unbiased parameter estimates computed which thus enable the predictive controller 690 to perform self-adaptation by adapting its own predictive model accordingly. This is accomplished by re-estimating the changing parameters of the model using only the more recent data measured from the patient.

FIG. 7 illustrates a diagrammatic representation of a system 700 for utilizing co-simulation of a physical model and a self-adaptive predictive controller using hybrid automata, depicted in the exemplary form of a computer system, in accordance with one embodiment. Such a system 700 utilizes a set of instructions, for causing the system or machine 700 to perform any one or more of the methodologies discussed herein, may be executed.

As described herein, the system seeks to determine how a controller behaves as its environment changes, thus, a simulation environment is created which emulates both a controller and a subject, such as a human patient. For instance, by way of example, the simulation environment simulates a controller such as the Artificial Pancreas exemplary controller described previously and additionally simulates a physical subject, such as the changing biometric characteristics of a human body or a diabetic patient. For the changing biometric characteristics of a human body, such a simulation environment may specifically model a human physical subject's glucose level in the blood over time due to changes associated with food consumption, exercise, emotions, etc.

In such an example, the human is the physical subject being modeled which persistently changes and the simulation environment accepts and accounts for those changes. The challenge is that a system cannot directly model the human, but the described system overcomes this problem by creating the simulation environment and then exploring all the various states that can be reached by the human physical subject, within the simulated environment, so as to ensure that the derived model has attained all the necessary safety parameters. For instance, so as to ensure that the human physical subject operates within a safe range of blood glucose levels and does not reach a hypoglycemic state or a hyperglycemic state.

Because the system is utilizing a physical subject model to model the human, as the model changes responsive to input parameters based on the human subjects changing biometric characteristics, the model is then iteratively updated. Consequently, a hybrid model is derived representing both the physical subject (e.g., the modeled human) and also the model for the controller's interaction (e.g., the controller model). The controller's operations are equivalent to discrete computer operations that occur on a specifically known and thus discrete time, whereas the human represented by the physical model changes on a continuous and ongoing basis and is therefore neither discrete nor precisely predictable. The hybrid model accounts for such changing characteristics and thus permits safe operation of the controller's discrete functions for the human subject's continuously changing biometric characteristics.

In certain embodiments, the machine may be connected (e.g., networked) to other machines in a Local Area Network (LAN), an intranet, an extranet, or the public Internet, although such cloud based or network communications are not mandatory to fulfill the proper functioning of the feedback loop which supports the self-adapting control design which is described in detail above. Regardless, the artificial pancreas and its systems and operations may be implemented by such a machine 700 which is specially configured to perform its required functions.

The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 700 includes a processor 702, a main memory 704 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 718 (e.g., a persistent storage device including hard disk drives and a persistent database and/or a multi-tenant database implementation), which communicate with each other via a bus 730. Main memory 704 includes a controller simulation 724, such as an artificial pancreas, and a physical model simulation (e.g., modeling a human) 723 and generated hybrid automata 725 by which to explore the reachable states and ensure the controller operates within the permissible safe states for the physical model (e.g., human), in furtherance of the embodiments as described herein. Main memory 704 and its sub-elements are operable in conjunction with processing logic 726 and processor 702 to perform the methodologies discussed herein.

Processor 702 represents one or more processing devices such as a microprocessor, central processing unit, or the like. More particularly, the processor 702 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 702 may also be one or more special-purpose processing devices such as an application specific integrated circuit (ASIC), a field programmable gate array (FPGA), a digital signal processor (DSP), network processor, or the like. Processor 702 is configured to execute the processing logic 726 for performing the operations and functionality which is discussed herein.

The computer system 700 may further include a network interface card 708. The computer system 700 also may include a user interface 710 (such as a video display unit, a liquid crystal display, etc.), an alphanumeric input device 712 (e.g., a keyboard), a cursor control device 714 (e.g., a mouse), and a signal generation device 716 (e.g., an integrated speaker). The computer system 700 may further include peripheral device 736 (e.g., wireless or wired communication devices, memory devices, storage devices, audio processing devices, video processing devices, etc.).

The secondary memory 718 may include a non-transitory machine-readable storage medium or a non-transitory computer readable storage medium or a non-transitory machine-accessible storage medium 731 on which is stored one or more sets of instructions (e.g., software 722) embodying any one or more of the methodologies or functions described herein. The software 722 may also reside, completely or at least partially, within the main memory 704 and/or within the processor 702 during execution thereof by the computer system 700, the main memory 704 and the processor 702 also constituting machine-readable storage media. The software 722 may further be transmitted or received over a network 720 via the network interface card 708.

According to a particular embodiment, the machine 700 implements a self-adaptive predictive control system specially configured to perform the methodologies described herein. For example such machine 700 may therefore include a memory 704 to store instructions; a processor 702 to execute instructions stored within the memory; a physical model simulation 723 via which to generate an initial patient model with initial patient model settings (k1, k2, . . . , kn); a controller simulation 724 via which to execute a program that takes as input, the initial patient model settings as configuration parameters that specify at least a plurality of initial states, a sampling time, and any number of additional optional parameters; a physical model simulation 723 such as a human (e.g., and further operable in conjunction with the physical environment predictive model at element 696 of FIG. 6D) each being operable in conjunction with the memory and processor of the machine 700 via which to receive new patient inputs responsive to executing the program with the initial patient model with the plurality of initial states; in which the self-adaptive predictive control system embodied by the machine 700 is to generate hybrid automata 725 as a variation of the initial states by applying the new patient inputs to the initial patient model; the controller simulation to further compute, via the program, a plurality of reachable states derived from the hybrid automata and producing an output file containing all reachable states computed; in which the self-adaptive predictive control system is to detect a change has occurred within the self-adaptive predictive control system and responsively generating a new patient predictive model with new parameter settings (k'1, k'2, . . . , k'n); in which the self-adaptive predictive control system is to iteratively repeat the computing of the plurality of reachable states and producing additional output files for each iteration containing all reachable states computed until a termination criterion is satisfied; and in which the self-adaptive predictive control system is to form a final reach set from a union of all output files having therein all reachable states obtained with all controller configurations generated at runtime of the executing program as computed for every iteration.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims are to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A method performed by a self-adaptive predictive control system having at least a memory and a processor therein to execute instructions, wherein the method comprises:

generating an initial patient model with initial patient model settings ($k_1, k_2, \ldots, k_n$);

executing a program via the processor that takes as input, the initial patient model settings as configuration parameters that specify at least a plurality of initial states, a sampling time, and any number of additional optional parameters;

receiving new patient inputs responsive to executing the program with the initial patient model with the plurality of initial states;

generating hybrid automata as a variation of the initial states by applying the new patient inputs to the initial patient model;

computing, via the executing program, a plurality of reachable states derived from the hybrid automata and producing an output file containing all reachable states computed;

detecting a change has occurred within the self-adaptive predictive control system and responsively generating a new patient predictive model with new parameter settings ($k'_1, k'_2, \ldots, k'_n$);

iteratively repeating the computing of the plurality of reachable states and producing additional output files for each iteration containing all reachable states computed until a termination criterion is satisfied;

forming a final reach set from a union of all output files having therein all reachable states obtained with all controller configurations generated at runtime of the executing program as computed for every iteration; and outputting an insulin infusion rate $I_t$ determined from the new patient predictive model which avoids both a hypoglycemic condition and a hyperglycemic condition for the final reach set.

2. The method of claim 1, wherein the initial model file and the new patient predictive model file are stored by the system in XML compatible format.

3. The method of claim 1, wherein the sampling time is adaptively computed by reachability analysis support functions.

4. The method of claim 1, wherein the sampling time is manually selected.

5. The method of claim 1, wherein the sampling time is selected based on a requirement that a discrete transition must not occur between two consecutive sampling times.

6. The method of claim 1, wherein the final reach set of the self-adaptive control system is a union of all reachable states obtained with all controller configurations generated at runtime of the executing program.

7. The method of claim 1, further comprising:
generating a safety report specific to a human patient modeled by the new patient predictive model;
wherein the safety report indicates a quality metric for the new patient predictive model with the new parameter settings reported as probability of the new patient predictive model maintaining a safe state for the human patient represented by the new patient predictive model and a probability of the new patient predictive model avoiding an unsafe state specifically for the human patient represented by the new patient predictive model.

8. The method of claim 7:
wherein the new patient predictive model with the new parameter settings form a personalized controller model unique to the human patient represented by the new patient predictive model.

9. The method of claim 7:
wherein the probability of the new patient predictive model avoiding an unsafe state specifically for the human patient represented by the new patient predictive model corresponds to a probability of the human patient represented by the new patient predictive model avoiding a hypoglycemic condition and avoiding a hyperglycemic condition when administered insulin by an artificial pancreas operating in accordance with the new patient predictive model with the new parameter settings.

10. A self-adaptive predictive control system, comprising:
a memory to store instructions;
a processor to execute instructions stored within the memory;
a physical simulation model operable in conjunction with the processor and the memory of the self-adaptive predictive control system to generate an initial patient model with initial patient model settings ($k_1, k_2, \ldots, k_n$);

a controller simulation to execute a program that takes as input, the initial patient model settings as configuration parameters that specify at least a plurality of initial states, a sampling time, and any number of additional optional parameters;

a physical model simulation to receive new patient inputs responsive to executing the program with the initial patient model with the plurality of initial states;

wherein the self-adaptive predictive control system is to generate hybrid automata as a variation of the initial states by applying the new patient inputs to the initial patient model;

the controller simulation to further compute, via the program, a plurality of reachable states derived from the hybrid automata and producing an output file containing all reachable states computed;

wherein the self-adaptive predictive control system is to detect a change has occurred within the self-adaptive predictive control system and responsively generating a new patient predictive model with new parameter settings ($k'_1, k'_2, \ldots, k'_n$);

wherein the self-adaptive predictive control system is to iteratively repeat the computing of the plurality of reachable states and producing additional output files for each iteration containing all reachable states computed until a termination criterion is satisfied;

wherein the self-adaptive predictive control system is to form a final reach set from a union of all output files having therein all reachable states obtained with all controller configurations generated at runtime of the executing program as computed for every iteration; and wherein the self-adaptive predictive control system is to output an insulin infusion rate $I_t$ determined from the new patient predictive model which avoids both a hypoglycemic condition and a hyperglycemic condition for the final reach set.

11. The system of claim 10, wherein the initial model file and the new patient predictive model file are stored by the system in XML compatible format.

12. The system of claim 10, wherein the sampling time is be adaptively computed by reachability analysis support functions.

13. The system of claim 10, wherein the sampling time is manually selected.

14. The system of claim 10, wherein the sampling time is selected based on a requirement that a discrete transition must not occur between two consecutive sampling times.

15. The system of claim 10, wherein the final reach set of the self-adaptive control system is a union of all reachable states obtained with all controller configurations generated at runtime of the executing program.

16. The system of claim 10:
wherein the self-adaptive predictive control system is to generate a safety report specific to a human patient modeled by the new patient predictive model;
wherein the safety report indicates a quality metric for the new patient predictive model with the new parameter settings reported as probability of the new patient predictive model maintaining a safe state for the human patient represented by the new patient predictive model and a probability of the new patient predictive model avoiding an unsafe state specifically for the human patient represented by the new patient predictive model.

17. The system of claim 16:
wherein the new patient predictive model with the new parameter settings form a personalized controller model unique to the human patient represented by the new patient predictive model.

18. The system of claim 16:
wherein the probability of the new patient predictive model avoiding an unsafe state specifically for the human patient represented by the new patient predictive model corresponds to a probability of the human patient represented by the new patient predictive model avoiding a hypoglycemic condition and avoiding a hyperglycemic condition when administered insulin by an artificial pancreas operating in accordance with the new patient predictive model with the new parameter settings.

19. Non-transitory computer readable storage media having instructions stored thereupon that, when executed by a processor of a self-adaptive predictive control system, the instructions cause the processor, to perform operations comprising:
generating an initial patient model with initial patient model settings ($k_1, k_2, \ldots, k_n$);
executing a program that takes as input, the initial patient model settings as configuration parameters that specify at least a plurality of initial states, a sampling time, and any number of additional optional parameters;
receiving new patient inputs responsive to executing the program with the initial patient model with the plurality of initial states;
generating hybrid automata as a variation of the initial states by applying the new patient inputs to the initial patient model;
computing, via the executing program, a plurality of reachable states derived from the hybrid automata and producing an output file containing all reachable states computed;
detecting a change has occurred within the self-adaptive predictive control system and responsively generating a new patient predictive model with new parameter settings ($k'_1, k'_2, \ldots, k'_n$);
iteratively repeating the computing of the plurality of reachable states and producing additional output files for each iteration containing all reachable states computed until a termination criterion is satisfied;
forming a final reach set from a union of all output files having therein all reachable states obtained with all controller configurations generated at runtime of the executing program as computed for every iteration; and
outputting an insulin infusion rate $I_r$ determined from the new patient predictive model which avoids both a hypoglycemic condition and a hyperglycemic condition for the final reach set.

20. The non-transitory computer readable storage media of claim 19, wherein the instructions cause the processor to perform operations further including:
generating a safety report specific to a human patient modeled by the new patient predictive model;
wherein the safety report indicates a quality metric for the new patient predictive model with the new parameter settings reported as probability of the new patient predictive model maintaining a safe state for the human patient represented by the new patient predictive model and a probability of the new patient predictive model avoiding an unsafe state specifically for the human patient represented by the new patient predictive model;
wherein the new patient predictive model with the new parameter settings form a personalized controller model unique to the human patient represented by the new patient predictive model; and
wherein the probability of the new patient predictive model avoiding an unsafe state specifically for the human patient represented by the new patient predictive model corresponds to a probability of the human patient represented by the new patient predictive model avoiding a hypoglycemic condition and avoiding a hyperglycemic condition when administered insulin by an artificial pancreas operating in accordance with the new patient predictive model with the new parameter settings.

* * * * *